(12) United States Patent
Venturelli

(10) Patent No.: US 7,771,410 B2
(45) Date of Patent: Aug. 10, 2010

(54) PIPE HAVING AT LEAST A PORTION WITH A VARIABLE FLEXIBILITY

(75) Inventor: Andrea Venturelli, Roncadelle (IT)

(73) Assignee: Invatec S.r.l., Roncadelle (Brescia) (IT)

( * ) Notice: Subject to any disclaimer, the term of this patent is extended or adjusted under 35 U.S.C. 154(b) by 1299 days.

(21) Appl. No.: 10/531,466

(22) PCT Filed: Nov. 25, 2003

(86) PCT No.: PCT/IT03/00777

§ 371 (c)(1),
(2), (4) Date: Apr. 28, 2005

(87) PCT Pub. No.: WO2004/047899

PCT Pub. Date: Jun. 10, 2004

(65) Prior Publication Data

US 2006/0100571 A1    May 11, 2006

(30) Foreign Application Priority Data

Nov. 25, 2002   (IT)   ......................... BS2002A0107

(51) Int. Cl.
*A61M 25/00*    (2006.01)

(52) U.S. Cl. .................. 604/525; 604/524; 604/523
(58) Field of Classification Search .................. 604/526
See application file for complete search history.

(56) References Cited

U.S. PATENT DOCUMENTS 5,573,520 A * 11/1996 Schwartz et al. ............ 604/526
5,743,876 A *  4/1998 Swanson ................. 604/96.01

FOREIGN PATENT DOCUMENTS

| EP | 0215173 | 3/1987 |
| EP | 0778040 | 6/1997 |
| EP | 0937481 | 8/1999 |
| GB | 2319183 | 5/1998 |
| WO | 97/25914 | 7/1997 |
| WO | WO97/25914 | 7/1997 |

* cited by examiner

*Primary Examiner*—Nicholas D Lucchesi
*Assistant Examiner*—Pritesh Patel
(74) *Attorney, Agent, or Firm*—Shoemaker and Mattare

(57) ABSTRACT

Tube, in particular for the use in medical devices in the form of catheters for endoluminal operations, wherein in at least one portion of its wall there are obtained notches (either slits or grooves) such as to locally increase the flexibility of the tube. The notches are provided in at least one distal zone of said tube.

15 Claims, 8 Drawing Sheets

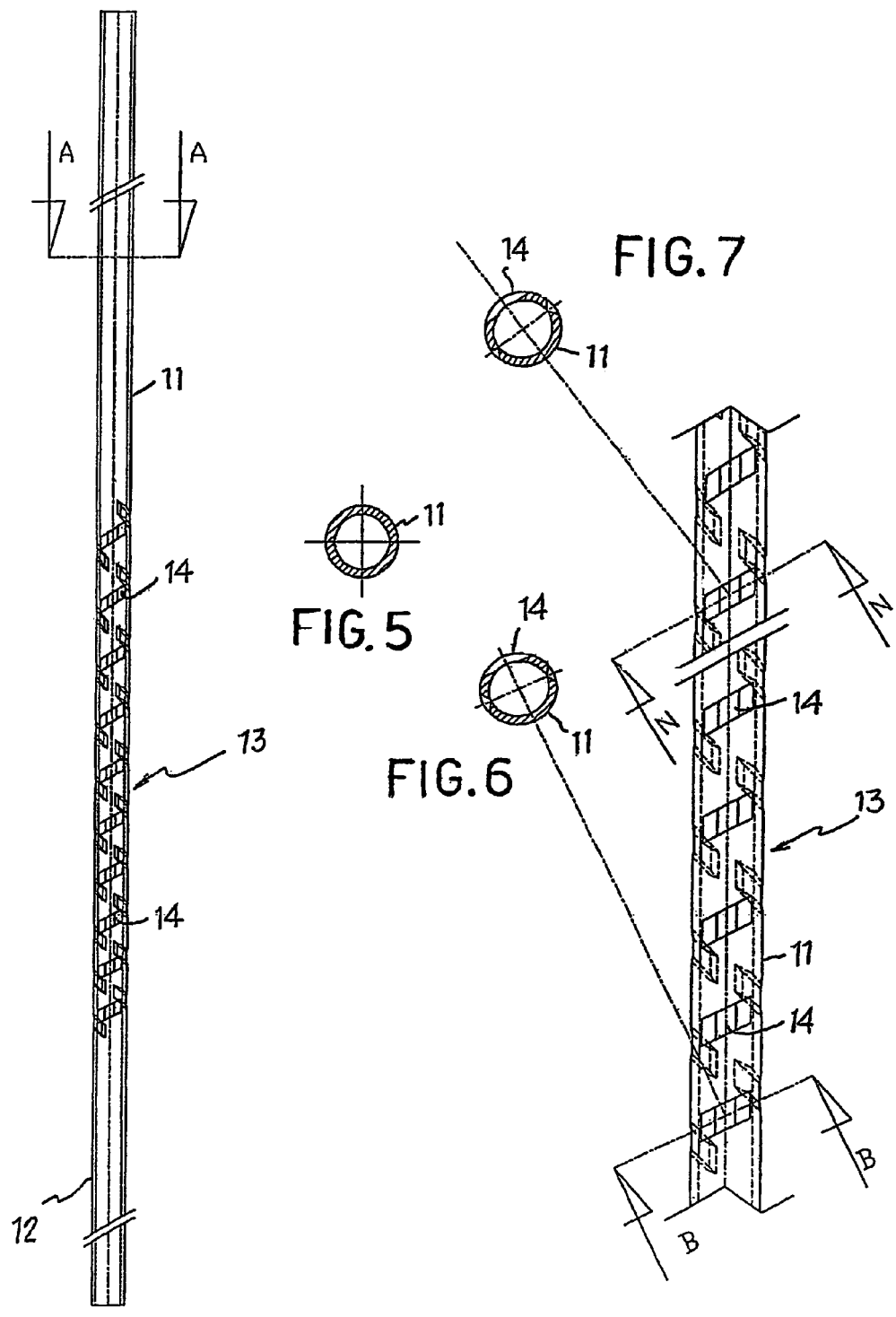

PIPE HAVING AT LEAST A PORTION WITH A VARIABLE FLEXIBILITY

TECHNICAL FIELD

The present finding relates to a tube for the use in medical devices in the form of catheters, especially but not particularly used in angioplasty operations.

BACKGROUND ART

The use of a metal tube for medical devices of the type considered herein is known. Since these devices must be capable of being introduced into a body through natural ducts up to the part to be treated, the tube used therein, at least in its forward or distal portion, must exhibit suitable flexibility to follow the turns of these ducts without damaging them.

Systems for rendering a stiff metal tube flexible have already been proposed, but they have been found capable of being improved further.

OBJECT OF THE INVENTION

The present finding therefore aims at proposing a metal tube obtained by an innovative method for rendering it flexible, which is simple, easy and inexpensive to be realised.

Correspondingly, the object is that of providing a tube configured in at least portion of its length to be more flexible than in the remaining portion of tube, particularly with a variable flexibility along the same portion, to facilitate its use in the aforementioned medical devices.

Another object of the invention is that of obtaining variation of flexibility to allow a gradual passage between the non-flexible portion of tube and the front portion or distal end so that the latter is very flexible.

A further object of the present invention is that of obtaining a tube having constant flexibility in any radial direction.

Such object and further purposes are achieved by a metal tube characterised in that in at least one portion of its wall there are obtained notches so as to increase the local flexion of the tube. According to the needs, the notches in the tube wall substantially exhibit a discontinuous helix shape pattern.

BRIEF DESCRIPTION OF THE DRAWINGS

Further features of the finding will appear more clearly from the following description made with reference to the attached indicative and non-limiting drawings, wherein:

FIG. 3 shows a schematic plane view of the tube of FIG. 1;

FIG. 4 shows an enlarged portion of FIG. 3;

FIG. 5 shows a cross section in the direction of arrows A A on FIG. 3;

FIGS. 6 and 7 show cross sections respectively according to arrows B B and N N on FIG. 4;

DETAILED DESCRIPTION OF PREFERRED EMBODIMENTS OF THE INVENTION

The tube proposed herein exhibits a wall 11 and, in a distal area 12, at least one portion 13 of its length which is rendered more flexible as compared to the tube's normal stiffness.

According to an embodiment, the more flexible portion 13 extends for a length comprised between 70 mm and 110 mm, preferably between 80 mm and 100 mm, measured starting from the distal end.

To render it more flexible, in the wall of such portion 13 of the starting tube there are obtained notches 14. The term "notch" means both a thorough slit that at least in one portion passes through the entire thickness of the tube wall, and a groove that in no portion passes through the entire thickness of the tube wall.

Such notches 14 are spaced out by full portions and exhibit, for example, a substantially discontinuous helical pattern. This helical pattern of notches 14 can be with one or more starts.

Figure 1:
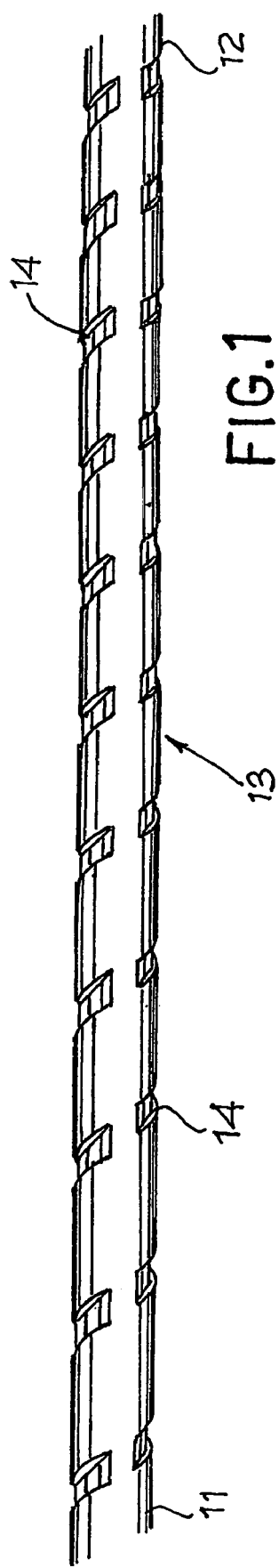
FIG. 1 shows a three-dimensional view of a piece of tube with a more flexible portion according to an embodiment.
Figure 2:
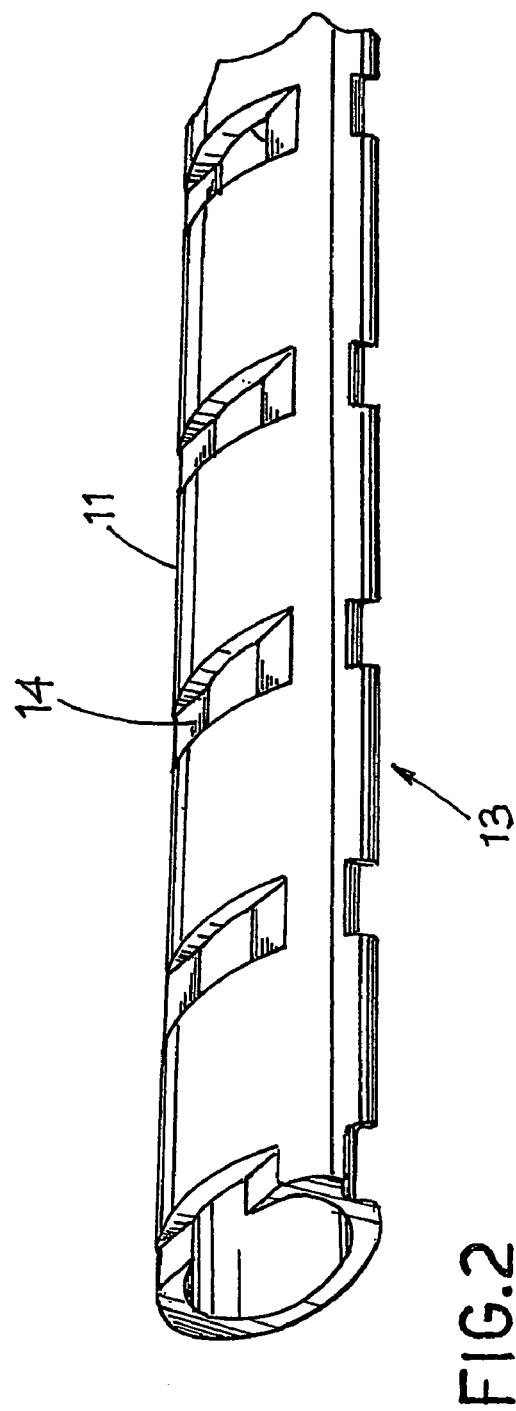
FIG. 2 shows an enlarged portion of the tube of FIG. 1.
Figure 8:
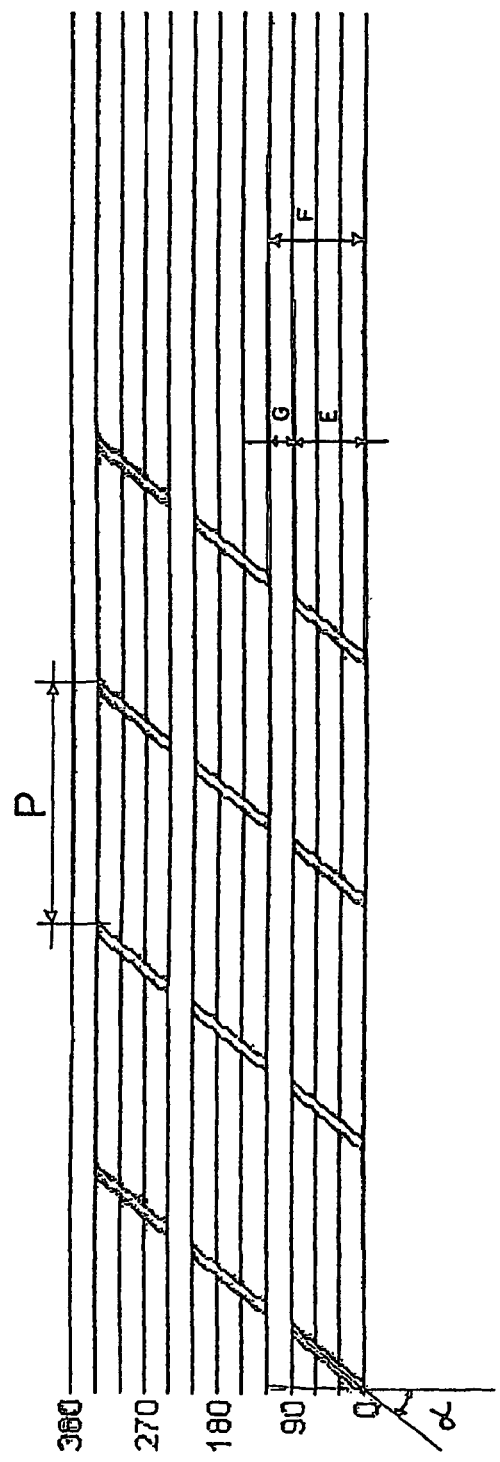
FIG. 8 shows the plane development of the cylindrical surface of the tube of FIG. 1.

If continuous flexibility is required along the entire portion 13, notches 14 for example are all the same by size and depth, and step P of their helical pattern is constant (FIG. 8).

However, to better satisfy the convenience of use and the performance of the tube used in a catheter, the flexibility of the portion 13 preferably is variable, to be higher in the vicinity of the distal end and decrease in the opposed direction.

According to an embodiment, a notch exhibits, at least for some portions of it, a prevailing longitudinal extension that determines a notch direction.

The flexibility of portion 13 can therefore be selected and realised in various manners. For example, it is possible to vary the inclination angle α of notches 14 between the notch direction and a circumference obtained on the outside surface of the tube and/or increase step P.

Or, it is possible to vary the depth of notches 14, for example the arc of removal of material from the tube wall 11, reducing it away from the distal end.

Similarly, the flexibility along the portion 13 can be varied by varying the width A of notches 14, also in this case by reducing it starting from the zone close to the distal end. The width A of the notches can be varied starting from a minimum (FIG. 15a) which is equal, for example, to the useful width of the cutting tool. According to a preferred embodiment, the minimum notch width is the typical width of a cut obtained by laser technology. Such minimum width therefore is comprised between about 5 μm and about 30 μm, preferably between about 10 μm and about 25 μm.

Figure 15:
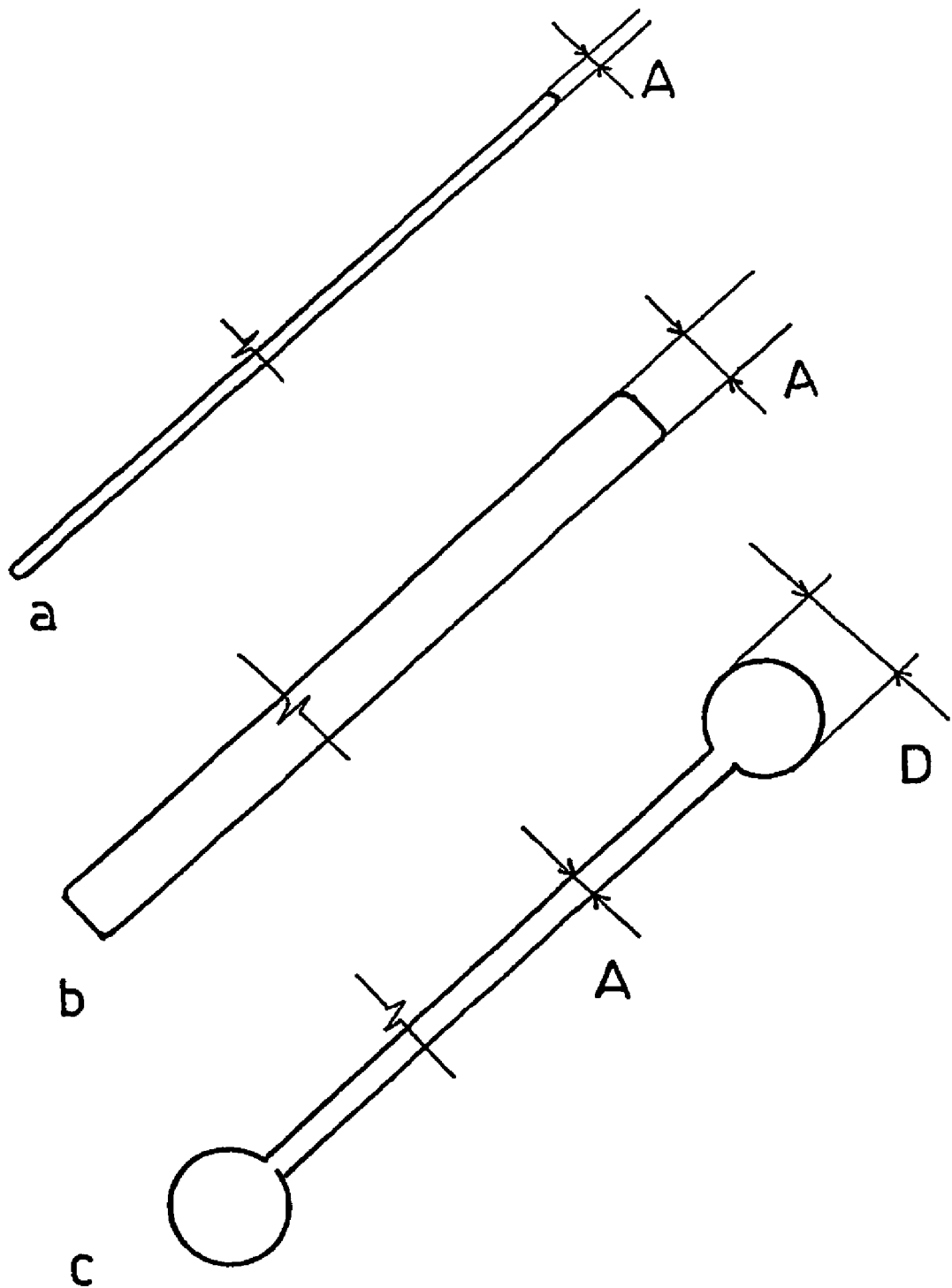
FIG. 15 shows some different possible geometries of the notches.

A larger width A can be obtained by a rectangular notch as that shown in FIG. 15b or with a parallelogram notch. A similar notch imparts higher deformability (both radial and axial) to the tube and reduces the over-tension or stress concentration effect that typically generates around the apices of a notch. The width of such notch can be as much as about 1 mm.

It is also possible, in order to reduce the stress concentration effect around the notch apex without having to increase the tube deformability, to use a cut geometry such as that shown in FIG. 15c, wherein the width A of the notch is determined on the basis of the flexibility needs of the tube, whereas the notch apices' stress concentrations are relieved by circular holes whose diameter D is larger than the width A of the notch.

According to a further embodiment, the flexibility along the portion 13 can be varied by thinning out notches 14 starting from the zone close to the distal end. As an alternative, a variable flexibility at the portion 13 can be obtained by applying a combination of two or more of the above systems, with reference to the shape, the arrangement and pattern of notches 14 in the tube wall.

Reference shall be made below to the figures from 8 to 11, which show the plane developments of the cylindrical outside surfaces of the portions 13 of the tube according to some embodiments.

FIG. 8 shows the plane development of the outside tube surface according to an embodiment. According to such embodiment, notches 14 are arranged with a constant inclination. The notches, for example, exhibit a width of about 90° and a reciprocal phase displacement of about 120°. The notch width is the measure of the arc that separates, on a circumference on the tube outside surface, the projection of the notch start from the projection of the notch end. The notch start and end are respectively defined as the distal end and the proximal end of the notch. The phase displacement F between the notches is the measure of the arc that on the same circumference separates the projection of the start of a first notch from the projection of the start of a second notch. If with E and phase displacement F are defined, it is also possible to define an angular distance G equal to the difference between phase displacement F and width E.

Figure 9:
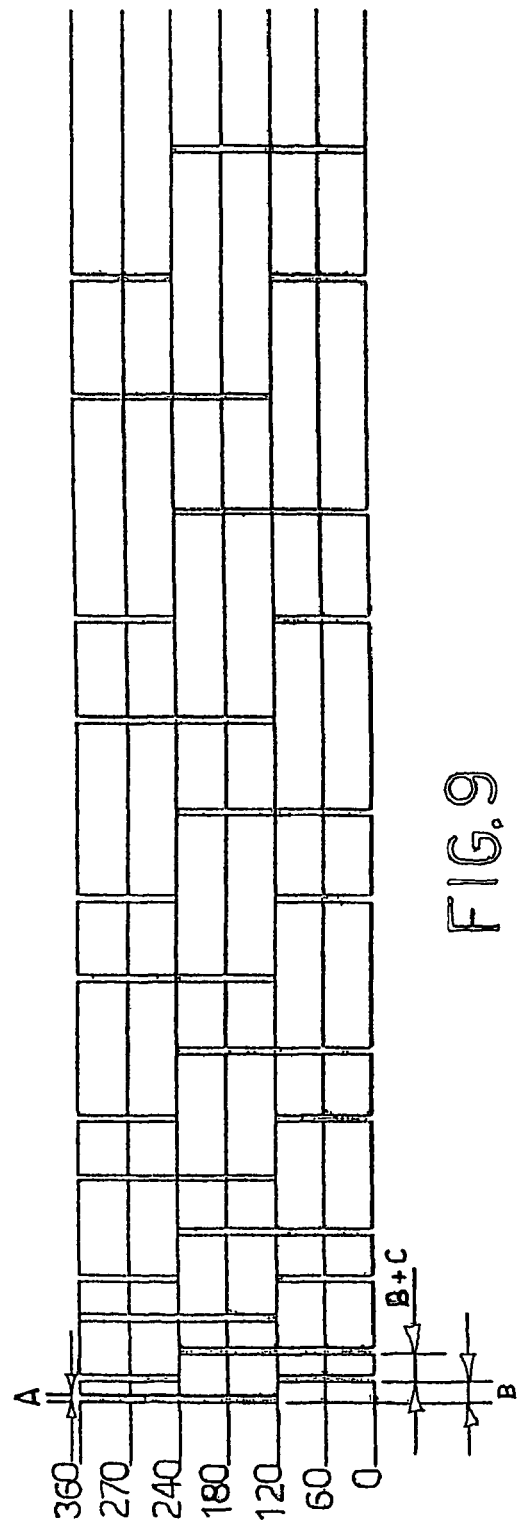
FIG. 9 shows the plane development of the cylindrical surface of the tube according to another embodiment.

FIG. 9 shows the plane development of the outside tube surface according to another embodiment. According to such embodiment, notches 14 are arranged with null inclination $\alpha$. In other words, the notches are perpendicular to the tube axis. The notches, for example, exhibit a width E of about 240° and a phase displacement F of about 120°. An expert of the art will promptly understand that in this embodiment it is not possible to keep the definition given above of "start" and "end" of the notch, since both ends are located at the same axial distance from the distal end. The expert of the art will also clearly see that in any case that it is possible to arbitrarily identify, in each notch, an end as start and the other end as end of the same notch.

According to a further embodiment, the axial distance between two consecutive notches starts from a value B and increases every time, for example by an amount C. Since proceeding from the distal end in a proximal direction the axial distance between the notches increases continuously, a very gradual passage is obtained in this embodiment from the flexibility of the non-machined tube to the distal end, which is the most flexible.

Figure 10:
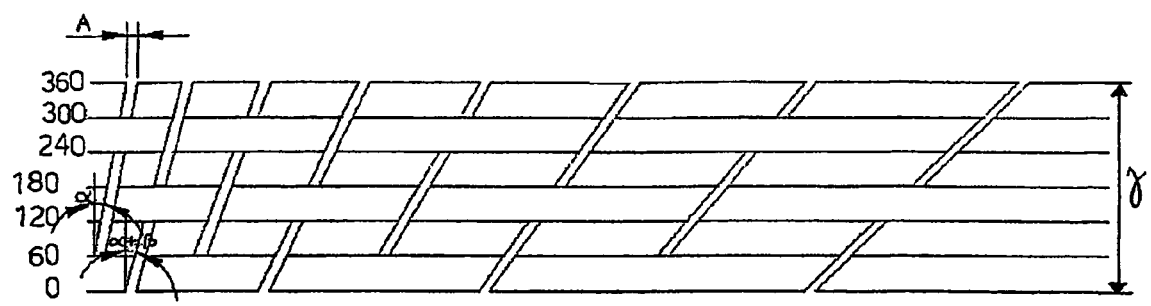
FIG. 10 shows the plane development of the cylindrical surface of the tube according to a further embodiment.

FIG. 10 shows the plane development of the tube outside surface according to a further embodiment. According to such embodiment, notches 14 are arranged with increasing step P and inclination. The inclination starts from a value $\alpha$ and increases by an amount $\beta$ at each arc $\gamma$ covered on an outside circumference in terms of width E of each notch and of angular distance G between two consecutive notches. According to the specific construction requirements, arc $\gamma$ can take measures comprised between 0° and 360°. In the example shown in FIG. 10, arc $\gamma$ measures 360°; in other words, the inclination of the notches is increased by an amount $\beta$ at each full revolution made on the outside surface of the tube in terms of notch width E and angular distance G.

Starting from the distal end in proximal direction, the notches have an increasing length but their width in degrees measured on an outside circumference of the tube is constant. For example, the notches have a width E of 180° and a phase displacement F of 240°. This particular embodiment allows obtaining, for the deformed tube, a very regular profile whose curvature varies continuously.

Figure 11:
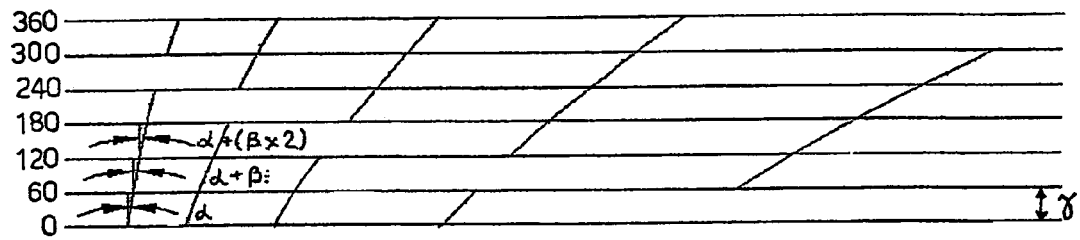
FIG. 11 shows the plane development of the cylindrical surface of the tube according to a further embodiment.
Figure 12:
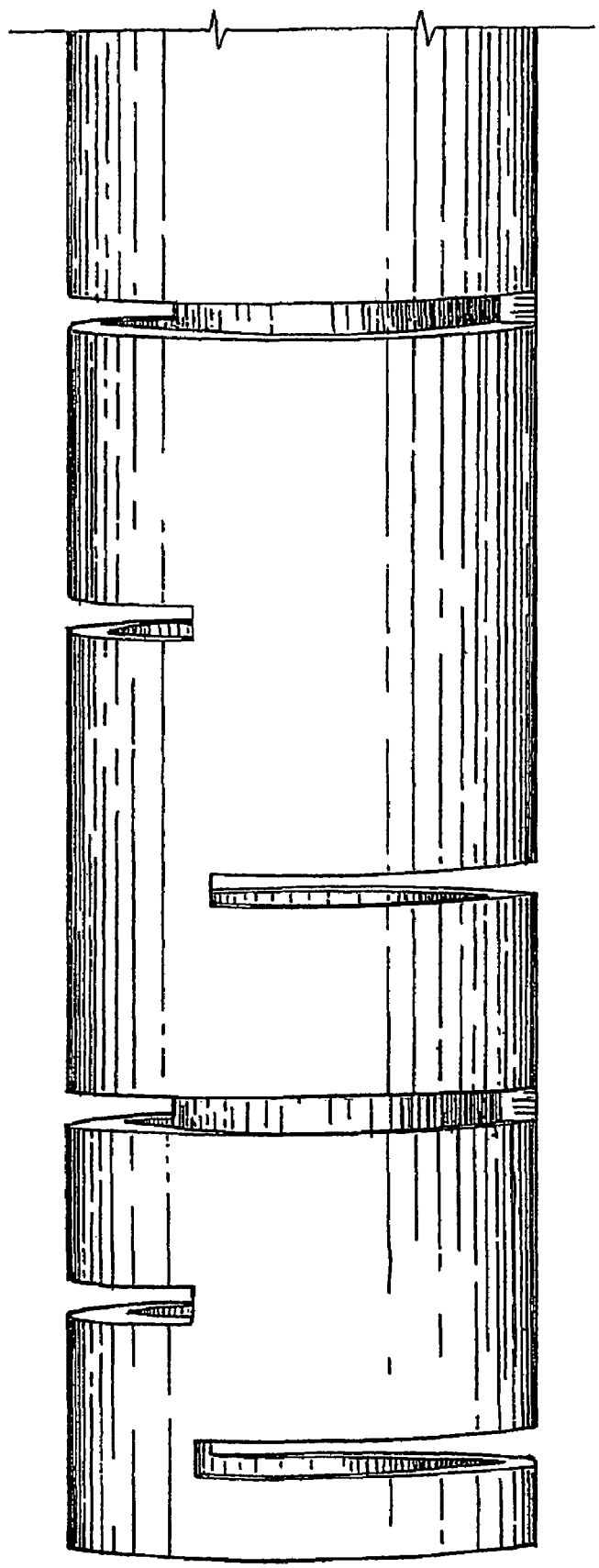
FIG. 12 shows a perspective view of the tube of FIG. 9.
Figure 13:
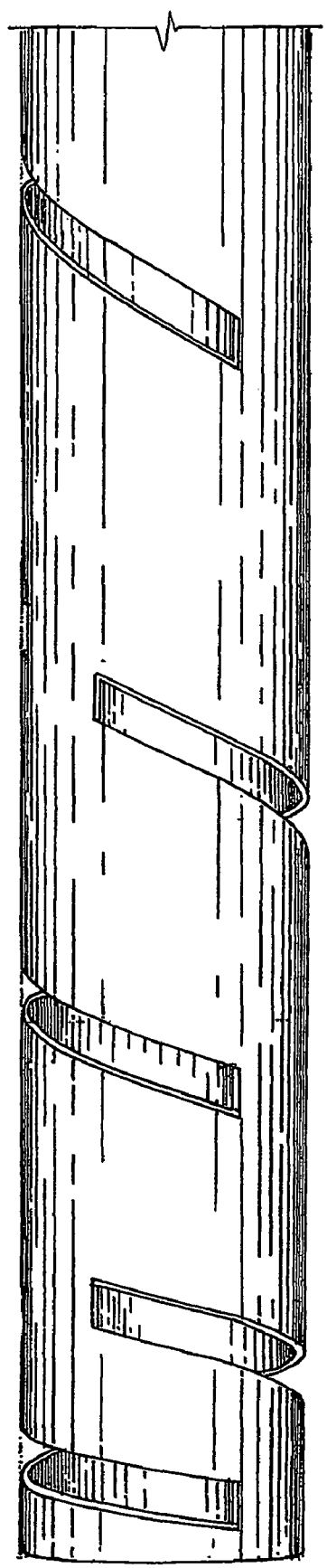
FIG. 13 shows a perspective view of the tube of FIG. 10.
Figure 14:
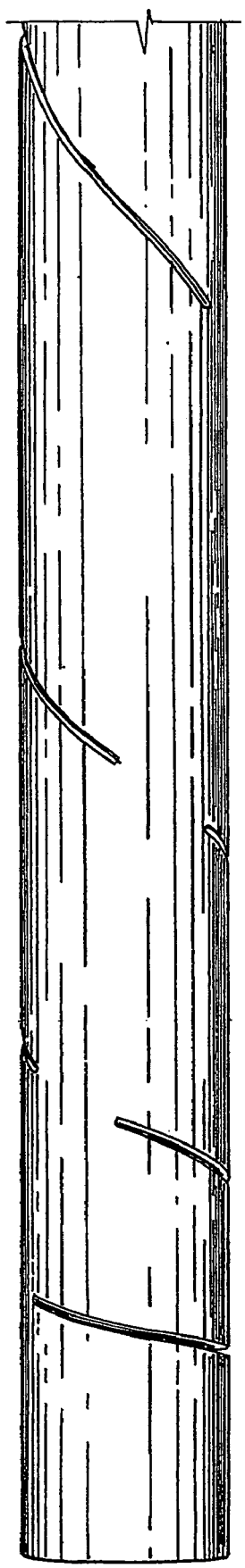
FIG. 14 shows a perspective view of the tube of FIG. 11.

FIG. 11 shows the plane development of the outside tube surface according to a further embodiment. According to such embodiment, notches 14 are arranged with increasing step P and inclination. In the example shown, arc $\gamma$ is of 60°; in other words, the notch inclination which at the beginning is equal to $\alpha$ is increased by an amount $\beta$ at each arc of 60° covered on the outside surface of the tube in terms of notch width E and angular distance G.

Starting from the distal end in proximal direction, the notches have an increasing length but their projection in terms of degrees on an outside circumference of the tube is constant. For example, the notches exhibit a width E of 240° and a phase displacement F of 300°. These special values allow obtaining a very even flexibility as the radial stressing direction varies. Moreover, this particular embodiment allows for obtaining, for the deformed tube, a very regular profile whose curvature varies continuously.

In the embodiments shown in FIGS. 10 and 11 it is possible to define an axial distance between consecutive notches. Such defines the distance that separates the projections of the respective starts of the notches on the axis or on a generatrix of the tube cylindrical surface. Note that also in these embodiments the axial distance between two consecutive notches increases from the distal end of the tube in proximal direction.

The tube according to the invention can be realised with metal materials, preferably with stainless steel, with polymeric materials or with composite materials.

According to a preferred embodiment, the tube surface is covered with a layer of polytetrafluoroethylene (PTFE), for example Teflon®, produced and marketed by Du Pont.

The fact that the tube is rendered flexible by a plurality of different and separate notches ensures a great residual resistance of the tube, along with an optimum flexibility.

Several changes, adaptations and replacements of elements with functionally equivalent ones can be made by one skilled in the art to the preferred embodiments described above without departing from the scope of the following claims.

The invention claimed is:

1. A medical tube for use as an endoluminal catheter, comprising a plurality of wall notches, at least one portion of its wall notches having a width A such as to locally increase flexibility of said tube, said notches being provided in at least one distal zone of said tube and exhibiting a substantially discontinuous helical pattern, wherein said notches form an angle $\alpha$ with a circumference obtained on an outside surface of said tube, said angle $\alpha$ increasing continuously from a distal end in a proximal direction, wherein each of said notches has two ends and a hole, having a diameter greater than the width of the notch, is formed at each said end to relieve stresses.

2. Tube according to claim 1, wherein said notches having a predetermined axial distance from one another.

3. Tube according to claim 2, wherein said axial distance between said notches increases from the distal end in the proximal direction.

4. Tube according to claim 1, wherein a width of said angle $\alpha$ increases by an amount $\beta$ at each arc $\gamma$ covered on the surface of the tube in terms of width E of each said notch and of angular distance G between two consecutive said notches.

5. Tube according to claim 4, wherein a measure of said arc $\gamma$ is between 0° and 360°.

6. Tube according to claim 1, wherein said width A is between 5 µm and 1 mm.

7. Tube according to claim 1, wherein said width A is between 10 μm and 25 μm.

8. Tube according to claim 1, wherein said portion comprising said notches extends from said distal end in a proximal direction for a length of between 70 and 110 mm.

9. Tube according to claim 1, wherein said portion comprising said notches extends from said distal end in a proximal direction for a length of between 80 and 100 mm.

10. Tube according to claim 1, wherein said tube is realized with a metal material.

11. Tube according to claim 10, wherein said metal material is stainless steel.

12. Tube according to claim 1, wherein said tube is made of a polymeric material.

13. Tube according to claim 1, wherein said tube is made of a composite material.

14. Tube according to claim 1, wherein said surface of said tube is covered with a layer of polytetrafluoroethylene (PTFE).

15. Catheter for endoluminal operations comprising a tube according to claim 1.

* * * * *

UNITED STATES PATENT AND TRADEMARK OFFICE
CERTIFICATE OF CORRECTION

PATENT NO. : 7,771,410 B2
APPLICATION NO. : 10/531466
DATED : August 10, 2010
INVENTOR(S) : Venturelli It is certified that error appears in the above-identified patent and that said Letters Patent is hereby corrected as shown below:

Title Page, item (75) Inventor should read as follows: Andrea Venturelli, Roncadelle --(Brescia)-- (IT)

Signed and Sealed this

Seventh Day of December, 2010

David J. Kappos
*Director of the United States Patent and Trademark Office*